United States Patent [19]

Nicklin

[11] Plant 5,095

[45] Aug. 30, 1983

[54] DISTINCT VARIETY OF APPLE TREE

[75] Inventor: John Nicklin, Marlboro, N.Y.

[73] Assignee: Hilltop Orchards & Nurseries, Inc., Hartford, Mich.

[21] Appl. No.: 309,580

[22] Filed: Oct. 8, 1981

[51] Int. Cl.[3] ..... A01H 5/03

[52] U.S. Cl. ..... Plt./34

[58] Field of Search ..... Plt./34

*Primary Examiner*—Robert E. Bagwill

*Attorney, Agent, or Firm*—John R. Nesbitt

[57] ABSTRACT

This invention relates to a limb mutation of a Cortland apple tree, but is distinguished from it because it develops its fruit color two weeks earlier and the fruit color is 90% red compared with 20–30% for Cortland.

2 Drawing Figures

DESCRIPTION OF THE INVENTION

This invention is a new and distinct cultivar of apple tree. It was discovered by applicant in a cultivated area at his farm located at 55 Mt. Zion Road, Marlboro, N.Y. 12542, as a limb mutation of a Cortland apple tree. The new variety was asexually reproduced by Hilltop Orchards & Nurseries Inc., and was given the experimental designation JN-64. Reproduction was both by budding and grafting from the parent limb and these trees are growing at the Hilltop Nurseries farm at RFD #2, Hartford, Mich.

The new variety colors two weeks earlier than Cortland, producing a mature fruit with 90% red color (5R 4/12 strong red Munsell hue color chart) compared to 20–30% red of the parent.

DESCRIPTION OF THE DRAWINGS

The accompanying drawing (color photograph) shows.

DETAILED DESCRIPTION OF THE NEW VARIETY

Tree

Figure 2:
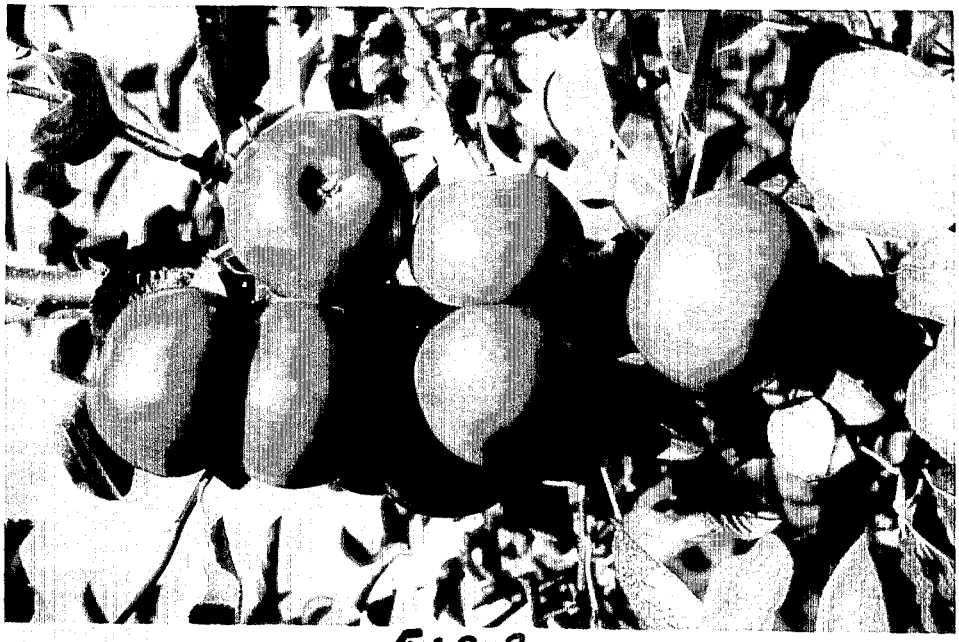
FIG. 2 shows a representative branch of JN-64 with mature fruit.
Figure 1:
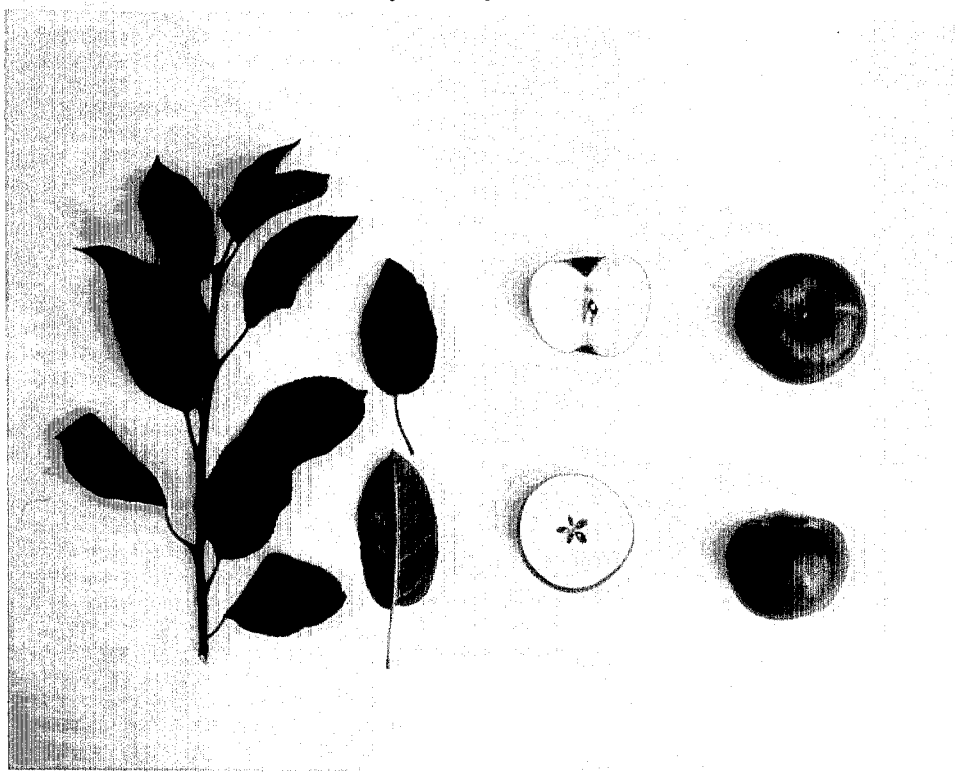
FIG. 1 shows a typical example of the fruit and foliage of JN-64.

Habit: Vigorous, somewhat straggly with an upright-spreading growth. It is productive, hardy, healthy and bears annually.

Bark: The shoots are long, nearly straight and medium in size with medium internodes. The bark is dark reddish to dark reddish olive colored. The lenticels are medium in number and size and are roundish, russet and slightly raised in character.

Leaf

The leaf is medium to large in size, flat, often downfolded. It is straight or slighty reflexed. The shape is broad oval to oblong with a medium green color and a spreading habit. The serrations are moderately dull, fairly regular and shallow with a dull surface that is rather rough with moderate pubescence.

Flowers

Blooms midseason, the same as standard Cortland. The petals are flat-oval shape with sepals short and slightly down-folded.

Fruit

Shape: The fruit is large, uniform, oblate and flat across the base that is slightly ribbed. The stem is variable in length and usually slender. The cavity is obtuse and slightly russeted. The basin is medium in depth and width, obtuse in shape. The calyx is small and party open.

Flesh: White, often with a pinkish tinge. The texture is fine, crisp, tender and juicy. It is subacid, aromatic and of very good quality. The white flesh oxidizes slowly on exposure to air and is slow to turn brown when cut.

Skin: The skin is tough, smooth and with much bloom. It has few lenticels that are small and numerous around the basin end.

Core: The core is of medium size, partly open with a clasping core-line. The calyx tubes are long and conical. The carpels are obovate and not tufted. The seeds are of medium size, wide, plump, obtuse to acute and numerous.

Color: The fruit colors two weeks before regular Cortland. The under color is greenish-yellow, overlaid with 90% bright dark red, glossy color, compared with a 20–30% red overcoat of regular Cortland fruit.

Maturity season: Same as Cortland (September 15 to October 1).

Keeping quality: Excellent both for long storage and shipping.

Use: This apple is good as a dessert apple, baking and commercial apple sauce.

I claim:

1. A new and distinct variety of apple tree substantially as described and illustrated in this application.

* * * * *